US009659360B2

(12) United States Patent
Hofsaess et al.

(10) Patent No.: US 9,659,360 B2
(45) Date of Patent: May 23, 2017

(54) IDENTIFYING AN ORIGINAL OBJECT IN A FORGERY-PROOF WAY

(71) Applicant: Georg-August-Universitaet Goettingen Stiftung Oeffentlichen Rechts, Goettingen (DE)

(72) Inventors: Hans Christian Hofsaess, Goettingen (DE); Kun Zhang, Bovenden (DE); Matthias Nagl, Goettingen (DE); Omar Bobes, Goettingen (DE)

(73) Assignee: GEORG-AUGUST-UNIVERSITAET GOETTINGEN STIFTUNG OEFFENTLICHEN RECHTS, Goettingen (DE)

( * ) Notice: Subject to any disclaimer, the term of this patent is extended or adjusted under 35 U.S.C. 154(b) by 404 days.

(21) Appl. No.: 14/190,773

(22) Filed: Feb. 26, 2014

(65) Prior Publication Data
US 2015/0243006 A1 Aug. 27, 2015

(51) Int. Cl.
*G06T 7/00* (2006.01)
*G01N 1/44* (2006.01)
(Continued)

(52) U.S. Cl.
CPC ............... *G06T 7/001* (2013.01); *A44C 17/00* (2013.01); *C23C 14/46* (2013.01); *G01N 1/44* (2013.01);
(Continued)

(58) Field of Classification Search
USPC .................................................. 382/100, 141
See application file for complete search history.

(56) References Cited

U.S. PATENT DOCUMENTS 5,521,984 A * 5/1996 Denenberg ......... G06K 9/00134
382/100
7,684,652 B2 * 3/2010 Zorab ....................... G07F 7/08
382/305
(Continued)

FOREIGN PATENT DOCUMENTS

EP 1 537 525 3/2004
EP 1 990 212 A1 11/2008

OTHER PUBLICATIONS

PCT International Search Report in co-pending, related PCT Application No. PCT/EP2015/053891, mailed Jun. 15, 2015.
(Continued)

*Primary Examiner* — Archene Turner
(74) *Attorney, Agent, or Firm* — Thomas | Horstemeyer, LLP (57) ABSTRACT

For identifying an original object comprising a surface essentially made of a first substance in a forgery-proof way, atoms of a second substance not soluble in the first substance are deposited on the surface. The surface is subjected to a beam of energized atoms providing movability to the atoms of the second substance in the surface to allow for a nucleation of a phase separation of a phase, in which the atoms of the second substance are concentrated. Then, an image of a surface pattern originating from the nucleation of the phase separation is taken and stored as a identifier for the original object. When a comparison image of a surface pattern of some object supposed to be the original object is compared to the identifier, the object is confirmed as being the original object, if the surface patterns in the identifier and the comparison image are identical.

20 Claims, 6 Drawing Sheets

(51) Int. Cl.
  *H01L 23/544* (2006.01)
  *G06K 9/62* (2006.01)
  *A44C 17/00* (2006.01)
  *G06K 19/06* (2006.01)
  *C23C 14/46* (2006.01)
  *G06K 9/00* (2006.01)

(52) U.S. Cl.
  CPC ..... *G06K 9/6201* (2013.01); *G06K 19/06084* (2013.01); *H01L 23/544* (2013.01); *G06K 9/00577* (2013.01); *G06T 2207/30108* (2013.01); *G06T 2207/30148* (2013.01); *H01L 2223/5442* (2013.01); *H01L 2223/54433* (2013.01); *H01L 2924/0002* (2013.01)

(56) References Cited

U.S. PATENT DOCUMENTS

| | | |
|---|---|---|
| 8,471,880 B2 | 6/2013 | Audouard et al. |
| 2001/0002315 A1 | 5/2001 | Schultz et al. |
| 2005/0019556 A1 | 1/2005 | Freeman et al. |

OTHER PUBLICATIONS

Zhang, K. et al.: "Designing self-organized nanopatterns on Si by ion irradiation and metal co-deposition" Nanotechnology, IOP, Bristol, GB, vol. 25, No. 8, Feb. 4, 2014, XP020257735, ISSN: 0957-4484.

"Fingerprints for Packaging: Surface Structure of Packaging Reveals Product Forgeries", website article located at: http://www.ipm.fraunhofer.de/content/dam/ipm/en/PDFs/Product%20sheet/PK/IMT%20Inline%20Measurement%20Techniques/Fraunhofer%20IPM_O-PUR_engl.pdf, (4 Pages), Dec. 2009.

http://www.holo-impact.de/files/Artikel_Explosive_accuracy_Fh-magazine_2-2008.pdf, Feb. 2008.

Zhang, K. et al.: "Surfactant-driven self-organized surface pattern by ion beam erosion", New Journal of Physics 13 (2011) 013033, Jan. 2011.

H. Hofsass et al.: "The role of phase separation for self-organized surface pattern formation by ion beam erosion and metal atom co-deposition" Appl Phys A (2013) 111:653-664, Jan. 2013.

\* cited by examiner

IDENTIFYING AN ORIGINAL OBJECT IN A FORGERY-PROOF WAY

FIELD OF THE INVENTION

The present invention generally relates to identifying an original object in a forgery-proof way. More particularly, the present invention relates to a method of identifying an original object in forgery-proof way by generating a surface pattern in a surface of the object and by imaging the surface pattern to provide for a identifier for the original object.

Further, the present invention relates to valuable products, like semiconductor products and jewelry products provided with a identifier.

BACKGROUND OF THE INVENTION

From http://www.holo-impact.de/files/Artikel_Explosive_accuracy_Fh-magazine_2-2008.pdf it is known to transfer delicate structures and even holograms onto metal surfaces by explosions copying a template into the surface. If the template comprises a hologram which is copied into the surface, the copied hologram may be used as a proof of originality in the same way as holograms are used on credit cards and banknotes, for example. However, this known method may as such be duplicated and even copied, i.e. two identical products may be produced which can not be distinguished from each other. Thus, it is impossible to say whether the one or the other of such two identical products has been involved in a particular event, for example.

A method and a device for marking a surface using controlled periodic nanostructures are known from U.S. Pat. No. 8,471,880 B2. According to this known method, an item of information is coded in the form of an image including values representative of the coded information. Then an area of the surface is marked dot by dot with a polarized laser beam to form oriented nanostructures on or in the surface by modulating the laser beam's polarization for each marking dot according to the value of a dot of the image. This known method may also be replicated providing for more than one object comprising the same marked surface.

From http://www.ipm.fraunhofer.de/content/dam/ipm/en/PDFs/Product%20sheet/PK/IMT%20Inline%20Measurement%20Techniques/Fraunhofer%20IPM_O-PUR_engl.pdf it is known to use surface structures of packaging to reveal product forgeries. This known method takes advantage of the fact that ink used in offset printing on packaging paper spreads individually according to the structure of the packaging paper. The characteristic spread pattern of the printing ink within the matrix structure of the packaging paper provides a characteristic fingerprint for each single packaging. This fingerprint is scanned with high resolution by a camera. The resulting data are stored in a data base. On an actual product, the fingerprint can be read with a hand scanner and checked for authenticity of the product within seconds. Via the internet the scanned fingerprint is compared with the fingerprints stored in the data base. However, a surface pattern or fingerprint which can be scanned and checked for authenticity by a camera even if only by a camera scanning with high resolution can also be copied by optical techniques. Suitable optical printing of photolithographic techniques may be complicated and may not be suitable for counterfeiting or plagiarizing of low or medium cost products. With high valuable products, however, these techniques may be interesting to the counterfeiters. This, for example, applies to high valuable electronics, aircraft components, jewelry and so on.

Zhang, K. et al.: "Surfactant-driven self-organized surface pattern by ion beam erosion", New Journal of Physics 13 (2011) 013033 report on the self-organized pattern formation on Si surfaces driven by Fe surfactant atoms. Si substrates were irradiated with 5 keV Xe ions at normal incidence under continuous deposition of Fe surfactant atoms. In the Absence of Fe deposition, uniform flat surfaces were obtained. With Fe surfactants, pronounced pattern, such as dots, combinations of dots and ripples and ripples with about 100 nm wavelength, were generated. Pattern formation is explained by ion-induced diffusion and phase separation of the initially flat amorphous $Fe_xSi$ layer and subsequent ion beam erosion with composition-dependent sputter yield.

H. Hofsäss et al.: "The role of phase separation for self-organized surface pattern formation by ion beam erosion and metal atom co-deposition" Appl Phys A (2013) 111:653-664 report the investigation of ripple pattern formation on Si surfaces at room temperature during normal incidence ion beam erosion under simultaneous deposition of different metallic co-deposited surfactant atoms. The co-deposition of small amounts of certain metallic atoms causes the evolution of nanoscale surface patterns on Si. Pronounced ripple pattern formation was found for co-deposited metals (Fe, Mo, Ni, W and Pt), which are prone to the formation of mono and disilicides. In contrast, for Cu and Au co-deposition the surface remains flat. Because of the very different behavior of Cu compared to Fe, Ni and Au compared to W, Pt, phase separation toward amorphous metal silicide phases is seen as a relevant process for the pattern formation in Si in the case of Fe, Mo, Ni, W, and Pt co-deposition.

There is still a need for a method of identifying an original object in fully forgery-proof way.

SUMMARY OF THE INVENTION

The present invention relates to method of identifying an original object in a forgery-proof way, the original object comprising a surface essentially made of a first substance. The method comprises selecting a second substance from the group of substances not soluble in the first substance, depositing atoms of the second substance at the surface, and subjecting the surface to a beam of energized atoms providing movability to the atoms of the second substance along the surface for a sufficient period of time to allows for a nucleation of a phase separation of a phase in which the atoms of the second substance are concentrated from the first substance in at least one defined area of the surface. After finishing the steps of depositing and subjecting, the method comprises taking at least one image of a surface pattern originating from the nucleation of the phase separation in the at least one defined area of the surface according to at least one defined imaging procedure, and storing the at least one image of the surface pattern taken according to the at least one defined imaging procedure as a identifier for the original object. The method further comprises taking at least one comparison image of a surface pattern in the at least one defined surface area of an object supposed to be the original object according to the at least one defined imaging procedure, comparing the comparison image to the identifier for the original object, and confirming the object as being the original object, if the surface pattern imaged in the identifier for the original object is identical to the surface pattern imaged in the comparison image.

The present invention also relates to a semiconductor product. The semiconductor product comprises a substrate essentially made of a semiconductor substance, the substrate comprising a surface pattern originating from a nucleation of a phase separation of a phase, in which metal atoms are concentrated, from the semiconductor substance in at least one defined area of its surface, the surface pattern comprising a coherence length of not more than 500 nm and extending over at least 3 coherence lengths in all surface directions.

The present invention also relates to a jewelry product. The jewelry product comprises a diamond essentially made of carbon, the diamond comprising a surface pattern originating from a nucleation of a phase separation of a phase, in which metal atoms are concentrated, from the carbon in at least one defined area of its surface, the surface pattern comprising a coherence length of not more than 500 nm and extending over at least 3 coherence lengths in all surface directions.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

The method according to the invention of identifying an original object having a surface essentially made of a first substance in a forgery-proof way comprises the selection of a second substance insoluble in the first substance. The insolubility of the second substance in the first substance may either mean that the second substance is not mixing with the first substance at all, or that it only mixes at one or more certain stoichiometric ratios, i.e. under formation of certain stoichiometric compounds.

The method according to the present invention further comprises depositing atoms of the second substance at the surface of the original object essentially made of the first substance. This step of depositing may be executed in various ways. Generally, it may be executed in any way providing a suitable amount of the second substance at the surface. For example, the second substance may be deposited by vapor deposition or sputter deposition on the surface. It may also be chemically or electro-chemically deposited on the surface, or atoms of the second substance may be implanted in the surface.

In the method of the present invention, the surface with the atoms of the second substances is subjected to a beam of energized atoms. These energized atoms are configured to provide movability to the atoms of the second substance along the surface, i.e. they have a suitable energy and they are provided at a suitable fluence for that purpose. This movability of the atoms of the second substance is provided for a sufficient period of time to allow for a nucleation of a phase separation of a phase in which the atoms of the second substance are concentrated from the first substance. This phase separation is driven by the insolubility of the second substance in the first substance and enabled by the movability of the atoms of the second substance due to the beam of energized atoms.

In the method according to the present invention, the phase separation does not go beyond a stage of nucleation. I.e., only nuclei of the phase in which the atoms of the second substance are concentrated are formed. Depending on the respective first and second substances, these nuclei may contain pure second substance or a stoichiometric compound of the first and second substances.

The nucleation of any phase separation is a stochastically determined process, i.e. a surface pattern originating from the nucleation of any phase separation is completely random. In other words, even two surface patterns originating from two phase separations taking place under exactly the same circumstances are different. This does, however, not exclude that the different surface patterns show common characteristics; they are, however, different and may thus be distinguished.

In fact, each surface pattern originating from the nucleation of the phase separation is unique and may thus be used for identifying an original object in whose surface the phase separation took place.

To make use of the fact that the surface pattern originating from a nucleation of any phase separation is unique, the method of the present invention comprises taking at least one image of the surface pattern. As the surface pattern is nanoscale, it will suitably neither cover the entire surface of the original object nor will the entire surface of the original object be imaged to take the at least one image of the surface pattern. Thus, the method of the present invention focuses on at least on defined area in which the surface pattern is both formed and imaged. Further, the method of the present invention makes use of a defined imaging procedure for taking the at least one image of the surface pattern as particularly images of nanoscale surface patterns are prone to variations with various imaging procedures.

The at least one image of the surface pattern taken according to the at least one defined imaging procedure is then stored as a identifier for the original object, and this identifier proves to be biunique.

So far as the term "biunique" is used here to describe the identifier for the original object, it means that the surface pattern imaged in the identifier is only found on one original object but no other object, and that there are no two different identifiers for the same original object. The latter aspect does, however, not exclude that the biunique identifier may be copied. It does also not exclude that the same biunique identifier may have various embodiments differing in size, surface position, imaging technique etc. If, however, all these variables are identical with two embodiments of the identifier, the two embodiments of the identifier are themselves identical.

Taking at least one comparison image of a surface pattern in the at least one defined surface area of an object supposed to be the original object according to the at least one defined imaging procedure then allows for deciding whether this object is indeed the original object. For this purpose, the comparison image is compared to the identifier for the original object, and only if the surface pattern in the identifier is identical to the surface pattern in the comparison image the object may be confirmed as being the original object.

The method of the present invention is forgery-proof for several reasons. As already explained, the surface pattern formed in the surface of the original object is completely random and thus always unique. It may also not be copied as it is impossible to purposefully arrange atoms of the second substance in the surface essentially consisting of the first substance in exactly the same way as they arranged themselves during the nucleation of a previous phase separation.

Further, the beam of energized atoms applied to provide movability to the atoms of the second substance along the surface essentially consisting of the first substance also causes an erosion of the surface which contributes to the surface pattern in the present invention. As a result, the surface pattern both includes a distribution of the nuclei of the phase in which the atoms of the second substance are concentrated and a height profile of the surface due to selective surface erosion. This still applies, if the height profile follows the distribution of the nuclei of the phase in which the atoms of the second substance are concentrated because of different erosion rates of the different phases.

Such a multi-component surface pattern may not be copied optically or photolithographically. Further optically or photolithographically copying the surface pattern is also hindered by the nanoscale dimensions of the surface pattern. Often the dimensions of the surface pattern will be well below the diffraction barrier that is an obstacle for higher spatial resolution in any optical and photolithographical methods.

The method of the present invention is particularly well suited for identifying original objects whose surface is made of a semiconductor substance. Thus, to the method of the present invention allows for identifying individual semiconductor components like, for example, semiconductor components of black boxes of aircrafts.

Generally, the first substance of which the surface of the original object is essentially made may be selected from silicon, cubic crystalline silicon, silicon dioxide, glass, quartz, aluminum oxide, sapphire, carbon or diamond. A lot of valuable and security-relevant products comprise surfaces essentially made of these substances and may thus be identified according to the method of the present invention.

The second substance has to be selected depending on the actual first substance. Generally, the second substance may be selected from metals. More particularly, it may be selected from Fe, Mo, Ni, Co, Ti, W, Pt, Cr, Mn, Ta, Hf, Ba, Ca, Y, Zr, U, Ga or any lanthanides. If the first substance, for example, is Si, the second substance may particularly be Fe, Mo, Ni, Co, Ti or Pt. In case of diamond or cubic crystalline carbon, the second substance may be Ti.

In case of sapphire, i.e. a crystal essentially made of $Al_2O_3$, or $SiO_2$ the second substance may particularly be Ga, Au, Ti, Zn, Mn, or Zr.

In the method according to the present invention, the steps of depositing and subjecting are preferably executed simultaneously, i.e. the atoms of the second substance are preferably co-deposited on the surface while subjecting the surface to erosion by the beam of energized atoms. For example, the atoms of the second substance may be sputter deposited in that energized atoms of the beam of energized atoms are also directed to a target located besides the surface or somewhere along the path of the energized atoms.

The amount of atoms of the second substance deposited at the surface has to be sufficient for the nucleation of the phase separation providing the surface pattern according to the present invention. When the atoms of the second substance are deposited by sputter deposition, for example, the concentration of the atoms of the second substance at the surface will quickly reach an equilibrium concentration, as the atoms of the second substance are also subject to the surface erosion by the beam of energized atoms. In the practice of the present invention, the absolute amount of atoms of the second substance deposited on the surface or the rate of atoms of the second substance sputter co-deposited on the surface proves not to be critical.

Typically, the goal of providing some movability to the atoms of the second substance along the surface is well achieved if the energized atoms are sufficient both in energy and fluence for transferring the first substance at the surface into an amorphous or disordered state. This is obviously no direct but an indirect measurement of suitable parameters of the beam of energized atoms.

In absolute values, the energized atoms may be provided at an energy of 0.1 to 100 keV per atom. More suitable energies are in a range of 0.2 to 50 keV, even more suitable values in a range of 1 to 10 keV. A typical suitable fluence is in the order of $10^{16}$ to $10^{18}$ energized atoms per square centimeter.

The beam of energized atoms may be oriented normal to the surface or at an angle to a normal to the surface selected from a range extending from 0° to 80°. The actual angle of the beam of energized atoms to the surface is not critical for forming any surface pattern according to the method of the present invention. The actual angle, however, will have an influence on the appearance of the actual surface pattern. With a small angle to the normal of the surface, the surface pattern will often mainly consist of dots indicating the phase in which the atoms of the second substance are concentrated. In case of a higher angle to the normal of the surface, the surface pattern will mainly consist of ripples extending across the direction of the beam of energized atoms. Whether the surface pattern essentially consist of dots or ripples is also determined by the direction in which the atoms of the second substance are co-deposited on the surface, for example.

The energized atoms of the beam of energized atoms may particularly include noble gas ions like, for example, xenon or argon ions, or nitrogen or oxygen ions, which may be energized, i.e. accelerated in an electric field.

The energized atoms of the beam of energized atoms may alternatively or additionally comprise atoms of the second substance. I.e., the atoms of the second substance may both be deposited on the surface and provide for the movability of the atoms of the second substance along the surface.

It should be noted that the term "atom" as used here does not only include electrically neutral or complete atoms but also electrically charged atoms, particularly ions lacking one or more electrons. Thus, the beam of energized atoms may particularly be an ion beam of energized ions.

It has been found by the inventors that the surface patterns formed according to Zhang, K. et al.: "Surfactant-driven self-organized surface pattern by ion beam erosion", New Journal of Physics 13 (2011) 013033, and H. Hofsäss et al.: "The role of phase separation for self-organized surface pattern formation by ion beam erosion and metal atom co-deposition" Appl Phys A (2013) 111:653-664, whose disclosures are incorporated herein by reference in their entireties display very short coherence lengths of some ten to some hundred nanometers. I.e., even within a surface pattern extending over a larger surface area and looking uniform, the sequence of the details of the surface pattern strongly vary from dot to dot or ripple to ripple. Particularly, no combinations of distances between neighboring dots or ribs are identical.

If the coherence length of the surface pattern gets in the order of or even below the diffraction barrier at the wavelengths of visible light, the details of the surface pattern become so fine that they can not be imaged with conventional microscopic procedures. Even with coarser details, the surface pattern nay not be reproduced by optical or photolithograpic structures, as the surface pattern consists of a combination of different phases of different compositions and different heights.

The size of the defined area of the surface of the original object which is sufficient for providing the biunique identifier when imaging the surface pattern typically extends over at least 3 coherence lengths in all surface directions. A greater size of the defined area will increase the security of the method according to the present invention but will also increase the effort in imaging the surface pattern and comparing the surface pattern in a comparison image to the identifier for the original object.

In the method of the present invention, the steps of depositing and subjecting may be executed in a vacuum chamber in which at least one step of manufacturing the original object is also executed. This may particularly apply to the manufacture of one or more semiconductor components as the original object. Both the standard manufacture of semiconductor components and the method of the present invention require a vacuum.

In the method of the present invention, the steps of depositing and subjecting may be executed at about room temperature, or at any temperature between about −100° C. and about 500° C.

The method according to the present invention, after the steps of depositing and subjecting and before the step of taking the at least one image of the surface pattern originating from the nucleation of the phase separation, may additionally comprise annealing the surface. During this step of annealing, the amorphous or disordered surface may become crystalline. In this way, the surface and the surface pattern may even become more stabilized with regard to subsequent thermal influences. In most cases, however, even the amorphous or disordered surface displaying the surface pattern is sufficiently stable over very long periods of time which are more than suitable for executing the method according to the present invention.

The defined area of the surface in which the surface pattern is formed and imaged for providing the identifier for the original object may be defined with regard to outer dimensions of the original object. It may also be identified by markers provided on the surface. Markers provided in a fixed spatial relation to the defined area of the surface may be applied to the surface as a sub-step of the method according to the present invention, i.e. with a part of a same apparatus also used for executing other steps of the method of the present invention.

The imaging procedure used in taking the picture of the surface pattern in the method of the present invention may be sensitive to a distribution of the second substance over the surface in the defined area of the surface. For example, the imaging procedure may basically provide a height profile of the surface structure, but this height profile may be distorted due to the sensitivity of the imaging procedure to the distribution of the second substance over the surface. In this way, the unique distribution of the atoms of the second substance over the surface has a double influence on the image taken and stored as the identifier for the original object. It influences the height distribution of the surface pattern over the surface as the first substance is typically more easily removed by erosion due to the energized atoms than the phase in which the atoms of the second substance are concentrated. Further, the non-homogenous distribution of the atoms of the second substance distorts the image of the surface pattern in a unique way.

Particularly, the imaging procedure used in the step of taking the image stored as the identifier for the original object and the comparison image may be or include atomic force microscopy, scanning tunneling microscopy or scanning electron microscopy. These imaging procedures are complex but reliable standard procedures. They may not be available at acceptable cost for imaging low value products. With high value products, however, they may be an absolutely acceptable means for identifying original objects. The imaging procedure may also include profilometry. Profilometry is not sensitive to a distribution of the second substance over the surface in the defined area of the surface, but It may be combined with electron probe micro analysis or X-ray microanalysis, for example, to additionally determine the composition of the surface in the defined area of the surface.

In the method of the present invention, the at least one defined imaging procedure may additionally include image processing. This image processing may be used to enhance the contrast of the surface pattern in the images, for example. This may allow for more easily comparing a comparison image to the identifier for the original object, even with slightly varying conditions of the imaging procedure, for example.

The step of storing the image taken of the surface pattern in the defined area of the surface of the original object may include storing the imaging procedure, particularly if different imaging procedures may be applicable.

The comparison of the comparison image with the identifier for the original object may include calculating at least one cross-correlation between the surface pattern imaged in the identifier and the surface pattern imaged in the comparison image. The decision whether the surface pattern imaged in the identifier for the original object and the surface pattern imaged in the comparison value are identical may then be based on whether a cross-correlation is at least as high as a predefined minimum value. With a sufficiently large defined surface area, the predefined minimum value may easily be set such that reaching the value only triggers the identification of the original object when there is no doubt that an object supposed to the original object really is the original object whereas all other objects are rejected.

In one embodiment, the present invention is used to identify a semiconductor product as the original object. In this case, the semiconductor product according to the invention comprises a substrate essentially made of a typical semiconductor substance like crystalline silicon. The substrate comprises a surface pattern which originates from a nucleation of a phase separation of a phase in which metal atoms are concentrated and which has separated from the semiconductor substance. The surface pattern is provided in a defined area of the surface of the substrate, comprises a coherence length of not more than 500 nm, and extends over at least 3 coherence lengths in all surface directions.

The semiconductor product according to the present invention may come with a data carrier comprising data providing access to an image of the surface pattern in the defined area of the surface, which has been taken according to a defined imaging procedure as a biunique identifier for the individual semiconductor product. The data carrier may directly comprise all data describing the biunique identifier. The data carrier may, however, only comprise data providing access to the biunique identifier stored in a data base. The minimum data on the data carrier indicate the name of the data base. It may be helpful to additionally include an indicator to the particular biunique identifier belonging to the original semiconductor product. However, it is no problem to search for the associated biunique identifier based on the comparison image taken of the actual semiconductor product for confirming its identity. The task of finding the matching biunique identifier for the semiconductor product according to the present invention may, for example, be solved by the same means used for identifying a person by DNA or an actual fingerprint found on a crime scene by comparison with respective entries in a criminal database.

As long as no manipulation of the biunique identifiers stored in the data base is possible, there is no need of limiting the access to the data base and the biunique identifiers stored therein. If a comparison image of some product is taken according to the defined imaging procedure and shows the same surface structure as some identifier in the data base, the product is confirmed as that original product associated with the particular identifier. This is simply a result of the biunique characteristics of the identifiers which each show a surface structure only found in the surface of one original product which has been previously imaged according to the defined imaging procedure to provide this particular identifier.

Semiconductor products according to the present invention may particularly include security-relevant semiconductor products, like components of aircraft electronics, and other high-value semiconductor products.

In another embodiment, the present invention is used to identify a jewelry product comprising a diamond. Diamonds essentially consists of crystalline carbon. A diamond of a jewelry product according to the present invention comprises a surface pattern originating from a nucleation of a phase separation of a phase in which metal atoms are concentrated. The surface pattern basically has the same characteristics as in case of the semiconductor product according to the present invention. The same applies to the data carrier which may come with the product.

Figure 1:
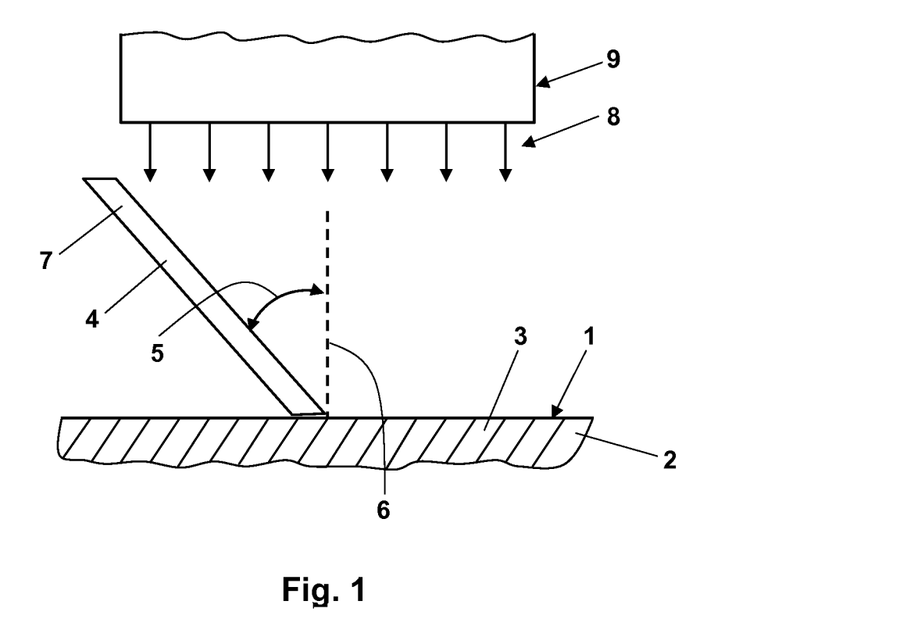
FIG. 1 illustrates a setup used in one embodiment of a method of identifying an original object according to the present invention for steps of depositing and subjecting.

Referring now in greater detail to the drawings, FIG. 1 shows a surface 1 of an object 2 made of a first substance 3 and a target 4 oriented at an angle 5 to a normal 6 to the surface 1 and consisting of a second substance 7. Here, the angle 5 is about 45°. Generally, the angle may be from about 10° to about 90°. The second substance 7 is selected from metals which are not soluble in the first substance 3 and which may form stoichiometric components with the substance 3. The substance 3, for example, is crystalline silicon or diamond. A beam 8 of energized atoms, particularly noble gas ions, like for example xenon or argon ions, is provided by an ion source 9 and directed normal to the surface 1. Generally, an angle between the beam 8 and the normal 6 to the surface 1 may be from 0° to about 80°. With the angle 5 getting close to 90°, the angle between the beam 8 and the normal 6 to the surface 1 should clearly differ from 0°. The energized atoms partially hit the target 4 and sputter deposit atoms of the substance 7 on the surface 1. Another part of the energized atoms hits the surface 1 and transfers it into an amorphous or disordered state. Further, due to subjecting the surface 1 to the energized atoms, the deposited atoms of the substance 7 are provided with some movability along the surface 1. This movability allows for a nucleation of a phase separation of a phase in which the atoms of the substance 7 deposited on the surface 1 are concentrated. In this way, the atoms of the substance 7 are separated from the remainder of the surface 1 and thus at least from the main part of the atoms of the substance 3. The nuclei of the phase in which the atoms of the substance 7 are concentrated may particularly be dot-shaped or ripple-shaped. Besides the nuclei of the phase separation, a surface pattern formed at the surface 1 due to the beam 8 of energized atoms also includes a height profile. This height profile is due to surface erosion by the energized atoms of the beam 8 hitting the surface 1. Typically, the removal of atoms of the substance 3 by the beam 8 of energized atoms takes place at a higher rate than the removal of the atoms of the substance 7 deposited on the surface 1 and of any atoms of the substance 3 forming stoichiometric compounds with the substance 7. Thus, the surface pattern typically consists of peaks or mountains at the positions of the separated phase and valleys between them.

As the surface pattern is formed by a nucleation of a phase separation, it is completely random and thus unique. This means that no two surface patterns formed are absolutely identical. Vice versa, an image of the surface pattern formed may thus be used to identify the object 2 by its surface pattern in a biunique way.

Figure 2:
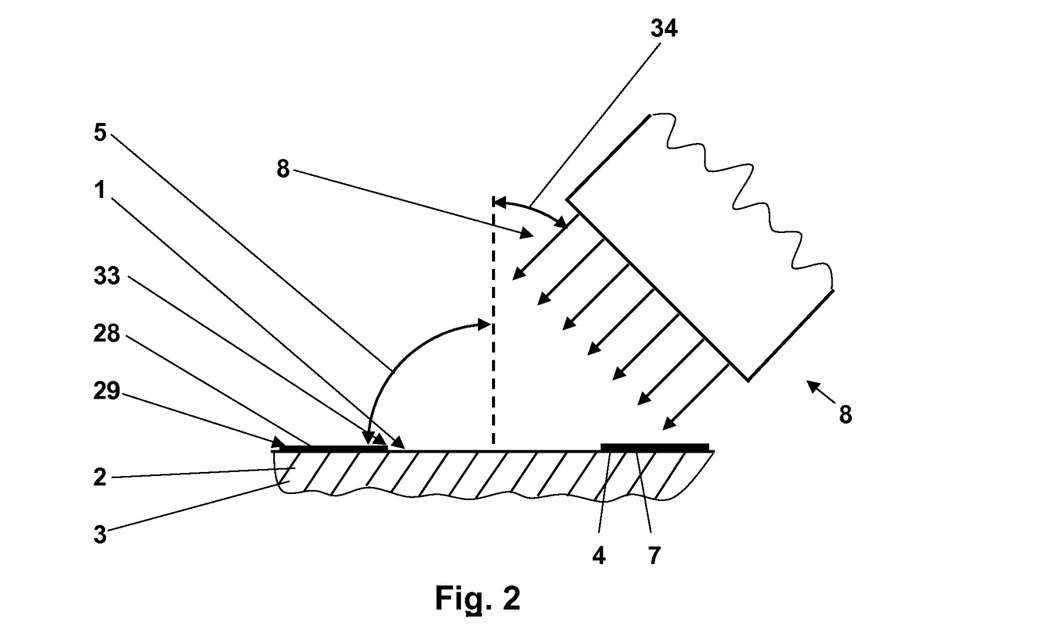
FIG. 2 illustrates another embodiment of a setup suitable for executing the steps of depositing and subjecting in the course of the method of the present invention.

FIG. 2 illustrates another embodiment of the arrangement of the target 4 made of the second substance 7 with regard to the surface 1. Here, the target 4 is a massive layer of the substance 7 previously deposited on the surface 1 outside a defined area 33 of the surface 1 in which the surface pattern is to be formed according to the present invention. Thus, the angle 5 of the target 4 with regard to the normal 6 is 90° here. To achieve the desired sputter deposition of atoms of the second substance 7 on the surface 1 made of the first substance 3, an angle 34 between the beam 8 and the normal 6 to the surface 1 is about 45° here. The massive layer of the substance 7 constitutes a frame 28 around the defined area 23 and thus serves as a marker 29 indicating the position of the defined area 33 in the surface 1. Instead of a massive layer of the substance 7 deposited on the surface 1, a separate mask made of the substance 7 may be placed on the surface 1 as the target 4. After removal of such a task, however, no marker remains indicating the defined area 33 in which the surface pattern has been formed according to the present invention.

Figure 3:
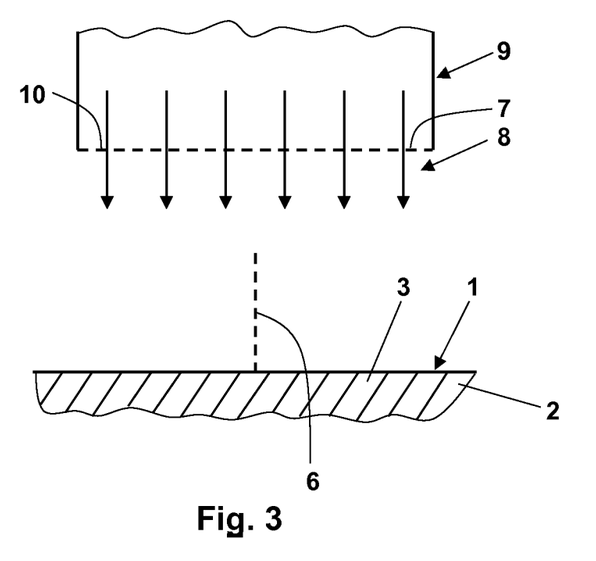
FIG. 3 illustrates a further embodiment of a setup suitable for executing the steps of depositing and subjecting in the course of the method of the present invention.

FIG. 3 illustrates another embodiment of the ion source 9 providing the beam 8 of energized atoms for depositing atoms of the substance 7 on the surface 1 of the object 2 essentially made of the substance 3. Here, no separate target 4 is provided, but a grid-shaped acceleration electrode 10 of the ion source 9 is made of the substance 7. Thus, some of the ions accelerated towards the electrode 10 hit the electrode 10, and the ions passing through the electrode 10 carry with them atoms of the substance 7 sputtered off the electrode 10. These atoms of the substance 7 are then deposited on the surface 1. In the same way as according to FIG. 1, some movability is provided to these atoms of the substance 7 along the surface 1 such that a phase separation of a phase in which these atoms of the substance 7 are concentrated may take place and form a surface pattern in the surface 1.

It is to be understood that the depictions of FIGS. 1 to 3 are purely schematic. A typical area of the surface 1 in which the surface pattern is formed only extends over some square micrometers. The intensity of the beam 8 of energized atoms may be in the order of $10^{17}$ ions per square centimeter. The energy of the individual atoms may be in the order of 0.1 to 1 keV with argon, and 2 to 5 keV with xenon. The surface pattern will then formed within a few seconds. The beam 8 of energized atoms only travels through vacuum. Thus, the steps indicated in FIGS. 1 and 2 have to be executed in a vacuum chamber to provide the surface 1 of the object 2 with the surface pattern. The steps indicated in FIGS. 1 and 2 may be executed at room temperature, or at any temperature between about −100° C. and +500° C.

Figure 4:
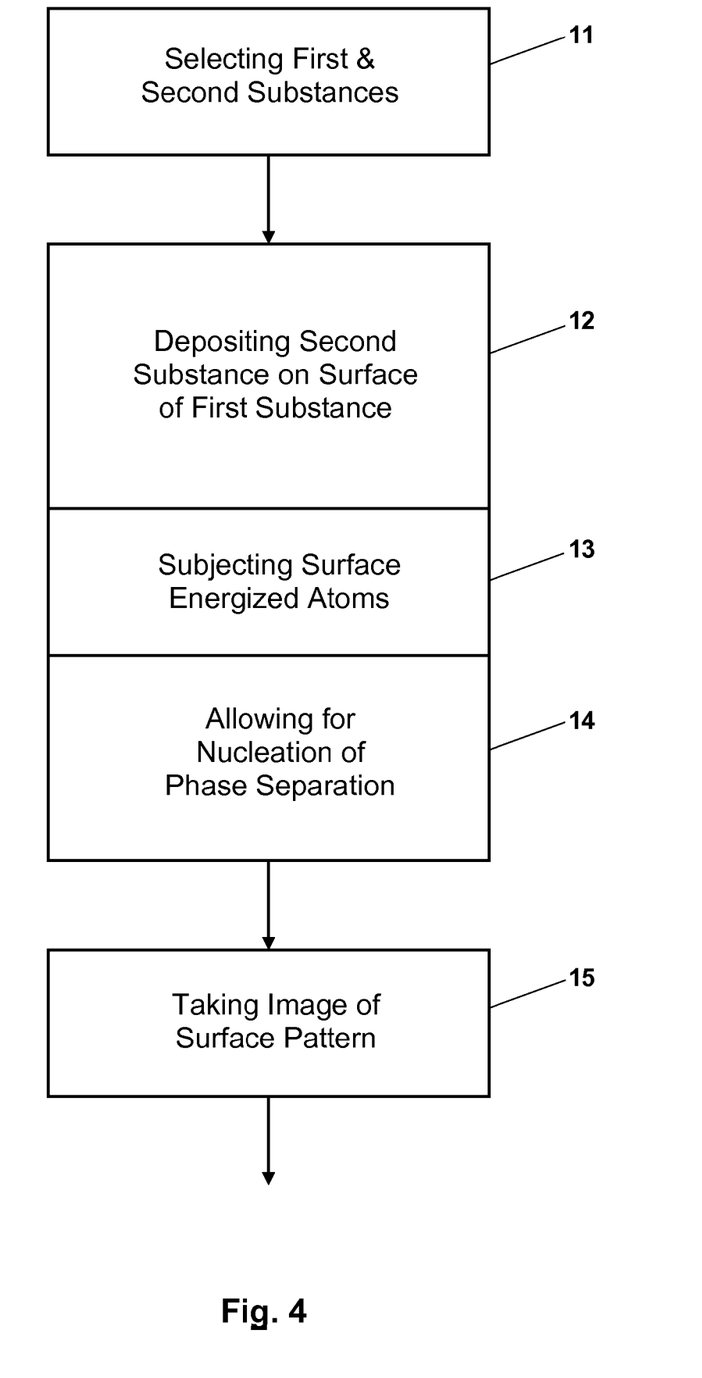
FIG. 4 is a flow chart of an embodiment of the method of the present invention.

The flow chart according to FIG. 4 starts with a step 11 of selecting the second substance 7 to be deposited on the surface 1 depending on the first substance 3 of the surface 1 such that there is a chemical driving force for a phase separation of a phase in which the second substance is concentrated from the first substance. Then, in a step 12, the selected substance 7 is deposited on the surface 1 made of the first substance 3. In a step 13, preferably occurring simultaneously, the surface is subjected to energized atoms, and this step 13 is continued for a sufficient period of time to allow for a nucleation of a phase separation in step 14.

Afterwards, in a step 15, an image is taken of the surface pattern formed in step 14 and also due to the surface erosion resulting from step 13. In step 16, this image is stored as a identifier for the object whose surface has been treated according to steps 12 to 14.

At some later point in time (indicated by a dashed line 17 between step 16 and next step 18), an object supposed to be the original object treated according to steps 12 to 14 may be confirmed as this original object by taking a comparison image in step 18. In step 19, this comparison image is compared to the image stored as the identifier. If both images show the same surface pattern, the object supposed to be the original object is confirmed as the original object in step 20.

The comparison carried out in step 19 may particularly be based on a calculation of a correlation between the images.

Figure 5:
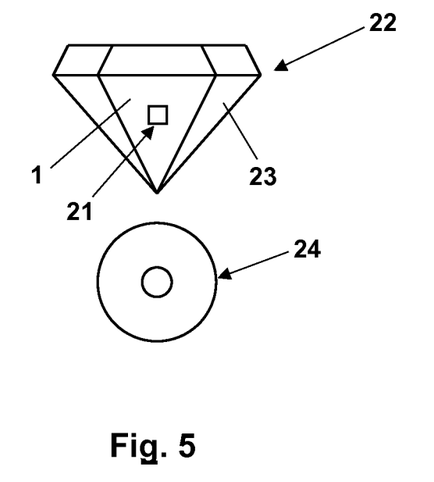
FIG. 5 shows a jewelry product according to the present invention.

FIG. 5 illustrates that the object treated according to steps 12 to 14 of FIG. 4, i.e. marked with a surface pattern 21, may, for example, be a jewelry product 22 comprising a diamond 23. The jewelry product further comprises a data carrier 24, here indicated as a compact disc. This data carrier comprises access data to access the identifier, i.e. the picture already taken of the surface pattern 21 of the original object. For confirming the jewelry product 22 as the only original object fitting to the identifier, the surface pattern 21 is to be imaged in the same way, i.e. according to the same imaging procedure used for providing the identifier, and then the two pictures are to be compared for the surface pattern imaged therein.

Figure 6:
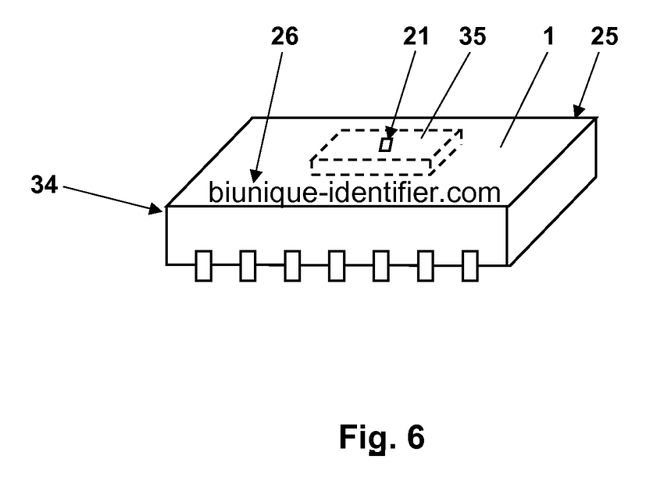
FIG. 6 shows a semiconductor product according to the present invention.

FIG. 6 illustrates that the object may also be a semiconductor product 25. Here, a housing 34 of the product 25 may be used as the data carrier indicating, for example, an internet address 26 where the identifier for the product 25 may be found. The surface pattern 21 according to the present invention is directly formed in the surface 1 of a die 35 made of crystalline silicon and included in the housing 34. A comparison image of the surface pattern 21 may only be taken after opening the housing 24 and taking the die 35 out of the housing. The comparison image will suitably be taken according to an imaging procedure described on the website identified by the internet address 26, and may then be uploaded to a data base also found via the internet address 26. In this way, it may be compared to all registered identifiers. This comparison may take place automatically and indicate the identity of the product 25, if a matching identifier is included in the data base.

Figure 7:
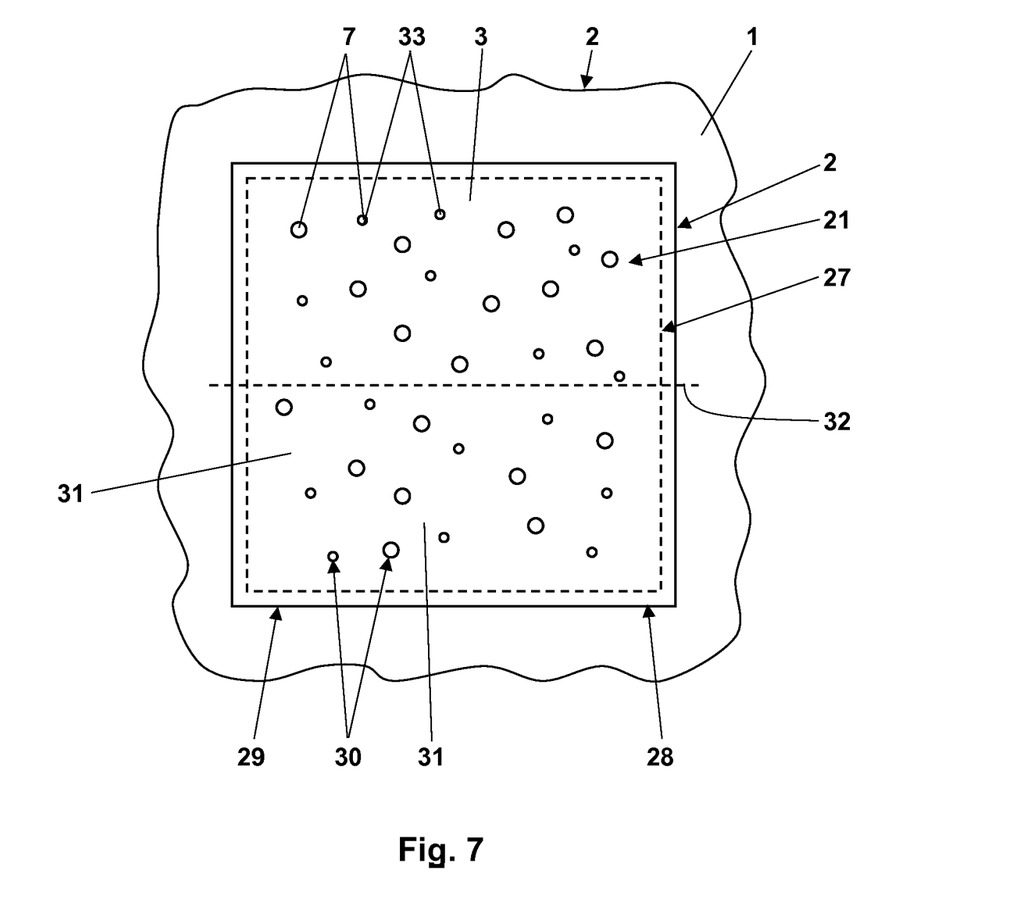
FIG. 7 shows an embodiment of an image of a surface pattern originating from a nucleation of a phase separation in a defined area of a surface of an original object to be identified according to the method of the present invention.
Figure 8:
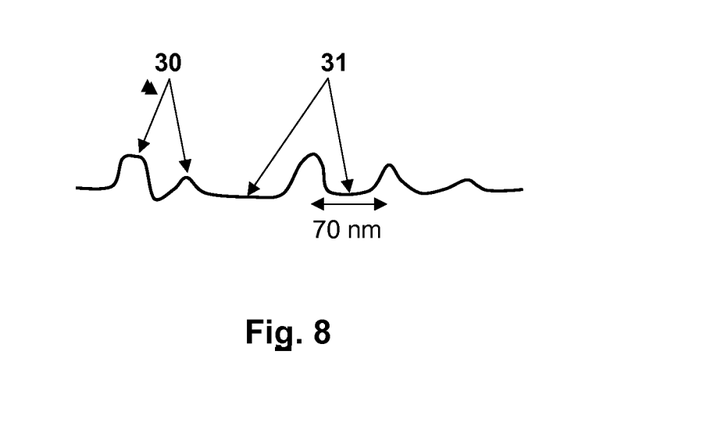
FIG. 8 shows a height profile through the surface pattern of FIG. 7, along a dashed line in FIG. 6.

FIG. 7 schematically shows a surface pattern formed in the surface 1 of an object 2 in a defined area 27 of the surface 1. The defined area 27 is enclosed by a frame 28 serving as a marker 29 marking the area of the surface in which the comparison picture of the surface pattern 21 is to be taken. The surface pattern basically consists of mountains 30 and valleys 31 between the mountains 30. These details are both found in the top view according to FIG. 7 and the height profile of FIG. 8 taken along the dashed line 32 in FIG. 7. The mountains 30 indicate the nuclei 33 of the phase in which the atoms of the second substance 7 are concentrated and which has been separated from the first substance 3. The valleys 31 are due to the higher rate at which the substance 3 has been eroded by energized atoms hitting the surface 1 as compared to the nuclei 33 of the phase in which the second substance 7 is concentrated.

These details 30, 31 of the surface pattern 21 are very fine, i.e. a typical spatial wavelength, i.e. a typical distance of the mountains 30 is only a few nanometers or a few 10 nanometers. Additionally, a coherence length of the surface pattern 21 determined by calculating an autocorrelation is just as long, see the data obtained by the inventors and disclosed in K. Zhang, et al.: "Designing self-organized nanopatterns on Si by ion irradiation and metal co-deposition" Nanotechnology 25 (2014) 085301 which is incorporated herein by reference in its entirety. As a result of both the small dimensions of these details 30 and 31 and the nature of the details, it is absolutely impossible to copy the surface pattern 21 formed by the nucleation of a phase separation in the surface 1.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of identifying an original object in a forgery-proof way, the original object comprising a surface essentially made of a first substance, the method comprising:
   selecting a second substance from the group of substances not soluble in the first substance;
   depositing atoms of the second substance at the surface,
   subjecting the surface to a beam of energized atoms providing movability to the atoms of the second substance along the surface for a sufficient period of time to allows for a nucleation of a phase separation of a phase in which the atoms of the second substance are concentrated from the first substance in at least one defined area of the surface;
   after finishing the steps of depositing and subjecting, taking at least one image of a surface pattern originating from the nucleation of the phase separation in the at least one defined area of the surface according to at least one defined imaging procedure;

storing the at least one image of the surface pattern taken according to the at least one defined imaging procedure as an identifier for the original object;

taking at least one comparison image of a surface pattern in the at least one defined surface area of an object supposed to be the original object according to the at least one defined imaging procedure;

comparing the comparison image to the identifier for the original object; and confirming the object as being the original object, if the surface pattern imaged in the identifier for the original object is identical to the surface pattern imaged in the comparison image.

2. The method of claim 1, further comprising selecting the first substance from semiconductors.

3. The method of claim 1, further comprising selecting the first substance from silicon, cubic crystalline silicon, silicon dioxide, glass, quartz, aluminum oxide, sapphire, carbon or diamond.

4. The method of claim 1, wherein the step of selecting the second substance comprises selecting the second substance from Fe, Mo, Ni, Co, Ti, W, Pt, Cr, Mn, Ta, Hf, Ba, Ca, Y, Zr, U, Ga or lanthanides.

5. The method of claim 1, wherein the steps of depositing and subjecting are executed simultaneously.

6. The method of claim 1, wherein the step of depositing comprises sputtering the second substance with energized atoms of the beam of energized atoms from at least one target.

7. The method of claim 1, wherein the step of subjecting comprises transferring the first substance at the surface into an amorphous or disordered state.

8. The method of claim 1, wherein the step of subjecting comprises providing the energized atoms at an energy of 0.1 keV to 100 keV.

9. The method of claim 1, wherein the step of subjecting comprises directing the beam of energized ions onto the surface at an angle to a normal of the surface selected from a range extending from 0° to 80°.

10. The method of claim 1, wherein the energized atoms in the step of subjecting are selected from noble gas ions, nitrogen ions, or oxygen ions.

11. The method of claim 1, wherein the energized atoms in the step of subjecting are atoms of the second substance.

12. The method of claim 1, wherein the step of subjecting comprises forming the surface pattern originating from the nucleation of the phase separation in the at least one defined area of the surface with a coherence length of not more than 500 nm, the at least one defined area of the surface extending over at least 3 coherence lengths in all surface directions.

13. The method of claim 1, wherein the steps of depositing and subjecting are executed in a vacuum chamber in which at least one step of manufacturing the original object is also executed.

14. The method of claim 1, further comprising defining the defined area of the surface with regard to outer dimensions of the original object.

15. The method of claim 1, further comprising providing markers on the surface defining the defined area of the surface.

16. The method of claim 1, wherein the at least one defined imaging procedure used in the step of taking is sensitive to a distribution of the second substance over the surface in the defined area of the surface.

17. The method of claim 14, wherein the at least one defined imaging procedure used in the step of taking comprises at least one procedure selected from atom force microscopy, scanning tunnel microscopy, scanning electron microscopy, or profilometry.

18. The method of claim 1, wherein the at least one defined imaging procedure used in the step of taking includes image processing.

19. The method of claim 1, wherein the step of storing includes storing the at least one defined imaging procedure.

20. The method of claim 1, wherein the step of comparing comprises calculating at least one cross-correlation between the surface pattern in the identifier for the original object and the surface pattern in the comparison image and deciding that the surface pattern in the identifier for the original object and the surface pattern in the comparison image are identical, if the at least one cross-correlation is at least as high as a predefined minimum value.

* * * * *